United States Patent
Chen et al.

(10) Patent No.: US 6,278,011 B1
(45) Date of Patent: Aug. 21, 2001

(54) POLYSILAHYDROCARBONS AS LUBRICANTS FOR AEROSPACE APPLICATION

(75) Inventors: Grace J. Chen, Fairborn; Carl Edgar Snyder, Jr., Trotwood; Kalathil Chandy Eapen, Beavercreek, all of OH (US)

(73) Assignee: The University of Dayton, Dayton, OH (US)

( * ) Notice: Subject to any disclaimer, the term of this patent is extended or adjusted under 35 U.S.C. 154(b) by 0 days.

(21) Appl. No.: 09/385,397

(22) Filed: Aug. 30, 1999

(51) Int. Cl.$^7$ ........................................................ C07F 7/08
(52) U.S. Cl. ........................... 556/465; 556/431; 556/435
(58) Field of Search ..................................... 556/431, 435, 556/465, 467, 478, 480

(56) References Cited

U.S. PATENT DOCUMENTS

| | | |
|---|---|---|
| 3,296,296 | 1/1967 | Webster . |
| 3,347,897 | 10/1967 | Webster . |
| 3,580,940 | 5/1971 | Webster . |
| 4,572,791 | 2/1986 | Onopchenko et al. . |
| 4,578,497 | 3/1986 | Onopchenko et al. . |
| 4,595,777 | 6/1986 | Bakshi et al. . |
| 4,711,966 | 12/1987 | Nelson . |
| 4,788,312 | 11/1988 | Paciorek et al. . |
| 5,026,893 | 6/1991 | Paciorek et al. . |

OTHER PUBLICATIONS

CA:67:107969 abs of J Organomet. Chem by Kuivila et al 10(1) pp 41–51, 1967.*
CA:122:227552 abs of JP07002878, Jan. 1995.*
CA:94:192397 abs of Dokl Akad Nauk SSSR 254(4) by Voronkov pp 887–90, 1980.*
CA:113:12954 abs of J Chromatogr by Defayes et al 500 pp 139–84, 1990.*
CA:122:191939 abs of Ind Eng Chem Res by Paciorek et al 34 (4) pp 1390–3, 1995.*
CA:105:134011 abs of J Organomet Chem by Boudjouk et al 296(3) pp 339–49, 1985.*
CA:83:79326 abs of Zh Obshch Khim by Voronkow et al 45(5) pp 1191, 1975.*
CA:112:139125 abs of Organometallics by Lewis et al 9(3) pp 621–5, 1990.*
CA:123:183184 abs of Inorg Chem by Lewis 34(12) pp 3182–9, 1995.*
CA:105:42907 abs of Zh Obshch Khim by Sheludyakov et al 55(8) pp 1795–9, 1985.*
Snyder, Jr., C.E. et al., "Synthesis and Characterization of Silahydrocarbons—A Class of Thermally Stable Wide–Liquid–Range Functional Fluids" ASLE Transactions, vol. 25, 3, May 11–14, 1981, pp. 299–308.

* cited by examiner

*Primary Examiner*—Jean F Vollano
(74) *Attorney, Agent, or Firm*—Killworth, Gottman, Hagan, Schaeff, LLP

(57) ABSTRACT

Two new classes of polysilahydrocarbons:

$$R_n\text{—Si—[CH}_2\text{CH}_2\text{—Si—R}^1{}_3]_{(4-n)} \quad (III)$$

$$C_6H_{(12-m)}[CH_2CH_2SiR^1{}_3]_m \quad (IV)$$

where R and $R_1$ are alkyl groups having from 1 to 18 carbon atoms, "n" is an integer between 0 and 3, and "m" is an integer between 2 and 6. Lubricant compositions containing the new polysilahydrocarbons are disclosed. Methods of making the new polysilahydrocarbons are also disclosed.

6 Claims, No Drawings

POLYSILAHYDROCARBONS AS LUBRICANTS FOR AEROSPACE APPLICATION

The U.S. Government has rights in this invention pursuant to Contract No. F33615-96-D-5052 awarded by the Department of the Air Force.

BACKGROUND OF THE INVENTION

This invention relates to new classes of polysilahydrocarbons and methods of making them. The invention also pertains to the application of such polysilahydrocarbons as synthetic lubricant base stocks. The term "polysilahydrocarbon" is used here to represent compounds containing more than one silicon atom in a molecule, including di-, tri-, tetra-, penta- and hexasilahydrocarbons depending on the specific number of silicon atoms in a molecule.

A wide variety of synthetic lubricant base stocks have been available for some time. These include esters, silicones, polyalphaolefins, trialkylated cyclopentane (Pennzane®) and the like. These base stocks are prepared by specific chemical synthesis methods rather than by refining of crude petroleum-based oils, and they offer distinct advantages over conventional mineral oils. These synthetic lubricant base stocks are particularly useful in aerospace and military applications which require performance at extremes of temperature, vacuum and hostile environments.

Among the various synthetic lubricant base stocks, tetraalkylsilanes, commonly referred to as silahydrocarbons, offer particular promise. A number of silahydrocarbons, particularly the monosilahydrocarbons, are described in U.S. Pat. Nos. 4,711,966, 4,595,777, 4,578,497 and 4,572,791 and references contained therein. The monosilahydrocarbons described by C. E. Snyder, Jr., et al., *ASLE Transactions*, Vol. 25, No. 3, pp. 298–308 (1982) have been shown to be superior to other classes of synthetic lubricant base stocks. For instance, they are superior to silicates in hydrolytic stability, lubricity and bulk modulus. They are also superior to polyalphaolefins in viscosity-temperature properties and thermal stability. The desirable effects of the silicon atom in a saturated hydrocarbon structure, as it exists in the monosilahydrocarbons referred to above, is well known to those familiar with the art. However, in applications requiring extremely low volatility, such as applications in the near-vacuum of space, these monosilahydrocarbons are not suitable. Useful monosilahydrocarbons are of relatively low molecular weight and would tend to "boil off" in the near vacuum of outer space. Therefore, higher molecular weight materials are required. One way of increasing the molecular weight of the monosilahydrocarbon is to increase the number of carbon atoms in the four alkyl residues attached to the silicon atom. This would lead to a very low ratio of silicon to carbon. It is likely that such materials would resemble high molecular weight hydrocarbons and would be waxy in nature rather than liquid. An alternate method of increasing molecular weights and thereby reducing volatility would be to have more than one silicon atom distributed in a high-molecular weight hydrocarbon structure. Such a structure would have the desired high molecular weight and at the same time possess the desirable liquid properties associated with the silicon atoms when present in a hydrocarbon structure.

Work in this direction has resulted in a series of compounds classified as di-, tri- tetra- and pentasilahydrocarbons. For example, some disilahydrocarbons are described in U.S. Pat. Nos. 3,296,296 and 3,347,897. For the preparation of some trisilahydrocarbons, see U.S. Pat. Nos. 4,788,312 and 3,580,940. U.S. Pat. No. 5,026,893 describes the synthesis and properties of a series of tetra- and pentasilahydrocarbons of the following general structures I and II, respectively:

$$R^1-Si[-R-Si(R^2R^3R^4)]_3 \qquad (I)$$

$$Si[-R-SiR^2R^3R^4]_4 \qquad (II)$$

where $R^1$, $R^2$, $R^3$ and $R^4$ represent alkyl groups having from one to 20 carbon atoms, and —R— represents an alkylene group having from three to 10 carbon atoms. While these inventions provide useful materials suitable for application in the near-vacuum environments of space, improvements in their properties and methods of preparation are desirable. For instance, base fluids having improved compatibility with known additive materials would be advantageous. In addition, the methods of synthesizing compounds having the general structures I and II involve multiple-step processes, which have the usual limitations and inefficiencies associated with such processes. More particularly, a Grignard reaction involving nine to 12 chlorines can result in an incomplete reaction leading to a product containing residual chlorine. Furthermore, a hydrosilylation step using a terminal olefin which can undergo isomerization leading to inactive internal olefins can result in an incomplete reaction. When high molecular weight terminal olefins isomerize, the internal olefins formed do not undergo hydrosilylation, resulting in high molecular weight impurities which are difficult to remove. Such impurities, when present in the lubricant, can outgas in space and result in contamination of sensitive components on board the spacecraft. Preparation of a material of high purity by this method is often difficult. Purification of the final product is of particular significance since these materials have extremely low vapor pressure and as a result, are not amenable to conventional means of purification such as distillation.

Therefore, there is a need for polysilahydrocarbons which have low volatility and good viscosity/temperature and wear properties. There is also a need for simple methods of synthesizing polysilahydrocarbons which are capable of providing high-purity products in high yield.

SUMMARY OF THE INVENTION

The present invention meets these needs by providing two new classes of polysilahydrocarbons:

$$R_n-Si-[CH_2CH_2-Si-R^1_3]_{(4-n)} \qquad (III)$$

$$C_6H_{(12-m)}[CH_2CH_2SiR^1_3]_m \qquad (IV)$$

where R and $R^1$ are alkyl groups having from 1 to 18 carbon atoms, "n" is an integer between 0 and 3, and "m" is an integer between 2 and 6.

In another aspect of the invention, the polysilahydrocarbons are used in lubricant compositions.

In another aspect of the invention, a process for making the new classes of polysilahydrocarbons is provided. An alkyl silane having a formula H—Si—$R^1_3$ is reacted with a compound containing at least one vinyl group having a formula selected from $R_n$—Si—$(CH=CH_2)_{(4-n)}$ and $C_6H_{(12-m)}(CH=CH_2)_m$, where R and $R^1$ are alkyl groups having from 1 to 18 carbon atoms, "n" is an integer between 0 and 3, and "m" is an integer between 2 and 6, in the presence of a catalyst. The catalyst can be a transition metal salt or a transition metal complex. The catalyst is preferably a platinum salt or a platinum complex, preferably platinum acetylacetonate.

In another aspect of the invention, another process for making the polysilahydrocarbons is provided. In this process, a chlorosilane having a formula $Cl_3$—Si—$CH_2CH_2$—Si—$Cl_3$ is reacted with an organometallic reagent having a formula RM, where R is an alkyl group having from 1 to 18 carbon atoms.

DESCRIPTION OF THE INVENTION

This invention provides two new classes of polysilahydrocarbon having the following general structures:

$$R_n\text{—Si—}[CH_2CH_2\text{—Si—}R^1{}_3]_{(4-n)} \quad (III)$$

$$C_6H_{(12-m)}[CH_2CH_2SiR^1{}_3]_{m} \quad (IV)$$

where R and $R^1$ represent alkyl groups having from one to 18 carbon atoms, and "n" and "m" are integers whose value ranges from zero to three for "n" and from two to six for "m". The alkyl groups can be unbranched or branched, although it is preferable that they be unbranched. The groups R and $R^1$ need not indicate a single alkyl group. Each group can also represent different alkyl groups leading to a multi-component product. Multi-component products are known to possess better low-temperature liquid properties than single component systems.

The number of silicon atoms can vary from two to six depending on the value of "n" and "m". For example, in a compound having the general structure III, if n=3, there would be two silicon atoms present, and the structure would represent a disilahydrocarbon. Similarly, if n=2, 1 or 0, the structure III would represent a tri-, tetra- or pentasilahydrocarbon, respectively. In compounds having the general structure IV, if m=3, there would be three silicon atoms present, and the structure would represent a tris-[trialkylsilylethyl]cyclohexane. The unique feature of these classes of polysilahydrocarbons is that two carbon atoms separate two silicon atoms in structure III and two carbon atoms separate the silicon atom from the cyclohexane ring in structure IV. The properties of these classes of polysilahydrocarbons can be adjusted by varying the proportions of the various substituent groups to achieve desired viscosity and vapor pressure values.

The poly-substituted cyclohexane (structure IV) has chiral centers so that stereoisomers are possible which can lead to good low temperature properties. Mixed compounds have lower freezing points, and consequently better flow properties at lower temperatures, as compared to pure compounds.

The polysilahydrocarbons of the present invention can be prepared by hydrosilylation or by the use of an organometallic reagent, depending on the type of the product desired. Both of these synthesis methods are well known to those familiar with the art. Hydrosilylation involves the addition of an alkylsilane containing an Si—H bond to another compound containing at least one vinyl group in the presence of a suitable catalyst. The following examples are illustrative.

(a) Hydrosilylation:

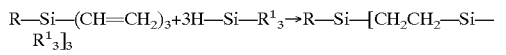

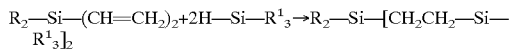

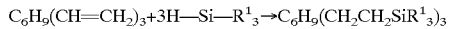

The use of a vinyl silane in hydrosilylation is particularly advantageous since unlike higher terminal olefins, there is no possibility of double-bond migration leading to internal olefins. If internal olefins are formed, they do not undergo hydrosilylation readily, and the reaction remains incomplete. As a result, it is difficult to purify the desired products. With the use of vinyl silanes, the hydrosilylation process goes to completion, giving rise to products of high purity.

A variety of transition metal salts and transition metal complexes are suitable as catalysts for hydrosilylation, and platinum salts and complexes are particularly suitable. Platinum acetylacetonate has been found to be an excellent catalyst.

The reaction of an organometallic reagent (RM) with a suitable chlorosilane is useful in certain cases as shown in the following example.

(b) Use of an organometallic reagent:

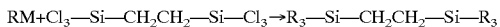

As mentioned earlier, in both these processes, a mixture of hydrosilanes and/or a mixture of an organometallic reagent containing different alkyl groups can be substituted for a pure material to obtain multi-component products.

The reactions can be performed at a temperature in the range of ambient to less than about 100° C. The time for the reaction to go to completion varies depending on the specific reactants used. This can be determined by known techniques, such as using $n\text{-}C_{12}H_{26}$ as an internal standard to determine the completion of the reaction by gas chromatographic analysis.

The starting materials required in these preparations are readily available commercially or they can be prepared by well-known reaction procedures. The synthesis of polysilahydrocarbons of the invention are illustrated below by specific examples.

EXAMPLE I

Synthesis of 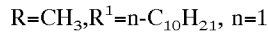

$R=CH_3, R^1=n\text{-}C_{10}H_{21}$, n=1

Into a two-liter, three-necked round-bottom flask equipped with a condenser, thermometer and kept under an atmosphere of dry $N_2$ gas, were placed $HSi(n\text{-}C_{10}H_{21})_3$ (733 g, 1.62 mole), $CH_3Si(CH=CH_2)_3$ (50.8 g, 0.409 mole), $n\text{-}C_{12}H_{26}$ (7.0 g, internal standard for GC analysis) and platinum (II) acetylacetonate (0.64 g, 1.62 mmole). The mixture was heated to ~45° C. Aliquot samples were removed periodically and analyzed by GC. After stirring at ~45° C. for several days in order to maximize the product, the reaction mixture was cooled, treated with petroleum ether (200 ml) and was passed through a column which was packed with silica gel (100 g, 60–200 mesh) on the top and aluminum oxide (200 g, activated, neutral, 150 mesh) on the bottom. It was eluted with petroleum ether until no more product was obtained. After removal of the solvent, a crude product was obtained. The crude product was distilled to remove the low boiling components at <290° C./~4×10⁵ mmHg and yielded the desired product (598 g, 99 percent yield, colorless liquid). The infrared spectrum was consistent with the expected structure of $CH_3Si[CH_2CH_2Si(n\text{-}C_{10}H_{21})_3]_3$. The product was analyzed for $C_{97}H_{204}Si_4$. The calculated amount was: C, 78.56; H, 13.86; Si, 7.58 percent, and the amount found was: C, 78.82; H, 13.55; Si, 7.74 percent.

EXAMPLE II

Synthesis of 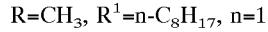

$R=CH_3$, $R^1=n\text{-}C_8H_{17}$, n=1

The reaction was set up and carried out as described in Example I using $(n\text{-}C_8H_{17})_3SiH$ (73.7 g, 200 mmole), $CH_3Si$ (CH=CH$_2$)$_3$ (6.22 g, 50.0 mmole) and Pt(acetlacetonate)$_2$ (79 mg, 0.20 mmole). After stirring at ~45° C. for eight days, the reaction mixture was worked up as before to obtain CH$_3$Si[CH$_2$CH$_2$Si(n-C$_8$H$_{17}$)$_3$]$_3$ (59.7 g, colorless liquid in 97 percent yield). The infrared spectrum and the fragmentation peaks of mass spectrum were consistent with the expected product. The product was analyzed for C$_{79}$H$_{168}$Si$_4$. The amount calculated was: C, 77.11; H, 13.76; Si, 9.13 percent. The amount found was: C, 77.14; H, 13.53; Si, 8.99 percent.

EXAMPLE III

Synthesis of R$_n$Si[CH$_2$CH$_2$SiR$^1$$_3$]$_{(4-n)}$

R=CH$_3$, R$^1$=n-C$_6$H$_{13}$, n=1

The reaction was set up and carried out as described in Example I using (n-C$_6$H$_{13}$)$_3$SiH (150.2 g, 529 mmole), CH$_3$Si(CH=CH$_2$)$_3$ (16.4 g, 132 mmole) and Pt(acetylacetonate)$_2$ (210 mg, 0.534 mmole). After stirring at ~45° C. for three days, the reaction mixture was worked up by the procedure described in Example I to obtain CH$_3$Si[CH$_2$CH$_2$Si(n-C$_6$H$_{13}$)$_3$]$_3$ (126.5 g, colorless liquid in 98 percent yield). The infrared and mass spectra were consistent with the expected structure. In the analysis for C$_{61}$H$_{132}$Si$_4$, the calculated amount was; C, 74.91; H, 13.60; Si, 11.49 percent, and the amount found was: C, 74.96; H, 13.62; Si, 14.44 percent.

EXAMPLE IV

Synthesis of R$_n$Si[CH$_2$CH$_2$SiR$^1$$_3$]$_{(4-n)}$ n=0, R$^1$=n-C$_8$H$_{17}$ The reactions of (n-C$_8$H$_{17}$)$_3$SiH (81.0 g, 220 mmole), Si(CH=CH$_2$)$_4$ (5.99 g, 44.0 mmole) Pt(acetylacetonate)$_2$ (87 mg, 0.22 mmole) were carried out as described in Example I. After stirring at ~45° C. for 12 days, the reaction mixture was worked up and produced, Si[CH$_2$CH$_2$Si(n-C$_8$H$_{17}$)$_3$]$_4$ (61.6 g, colorless liquid, 88 percent yield). The infrared spectrum was consistent with the expected structure. The product was analyzed for C$_{104}$H$_{220}$Si$_5$. The amount calculated was: C, 77.52; H, 13.76, Si, 8.72 percent, and the amount found was: C, 78.60; H, 13.71; Si, 8.62 percent.

EXAMPLE V

Synthesis of C$_6$H$_{(12-m)}$[CH$_2$CH$_2$SiR$^1$$_3$]$_m$ m=3, R$^1$=n-C$_6$H$_{13}$ The reactions of (n-C$_6$H$_{13}$)$_3$SiH (150.5 g, 530 mmole), C$_6$H$_9$(CH=CH$_2$)$_3$ (21.5 g, 132 mmole) and Pt(acetylacetone)$_2$ (200 mg, 0.51 mmole) were carried out as described in Example I. After stirring at ~55° C. for 18 days, the reaction mixture was worked up and produced C$_6$H$_9$[CH$_2$CH$_2$Si(n-C$_6$H$_{13}$)$_3$]$_3$ (128.5 g, colorless liquid in 96 percent yield). The infrared and HNMR spectra and the fragmentation peaks of mass spectrum were consistent with the expected structure. The analysis for C$_{66}$H$_{138}$Si$_3$ revealed a calculated amount of: C, 78.02; H, 13.69; Si, 8.29 percent, and the amount found was: C, 77.60; H, 13.90; Si, 8.40 percent.

EXAMPLE VI

Synthesis of R$_n$Si[CH$_2$CH$_2$SiR$^1$$_3$]$_{(4-n)}$

R=R$^1$=n-C$_{10}$H$_{21}$, n=3

The reaction was carried out in a similar manner as described in Example I. A mixture of (n-C$_{10}$H$_{21}$)$_3$SiH (25.0 g, 55.3 mmole), (n-C$_{10}$H$_{21}$)$_3$SiCH=CH$_2$ (26.4 g, 55.3 mmole) and Pt(acetylacetonate)$_2$ (22 mg, 5.53×10$^{-2}$ mmole) was placed in the flask. The reaction mixture was stirred at room temperature for two days and then at ~40° C. for another two days. The product was purified by column chromatography as described in Example I. After removal of the solvent, a crude product was obtained. The crude product was distilled to remove the low boiling components at <230° C./5×10$^{-5}$ mmHg and yielded the desired product (n-C$_{10}$H$_{21}$)$_3$SiCH$_2$CH$_2$Si(n-C$_{10}$H$_{21}$)$_3$ (48.4 g, colorless liquid, 94 percent yield). The infrared spectrum and mass spectra data were consistent with the expected structure. In the analysis for C$_{62}$H$_{130}$Si$_2$, the amount calculated was: C, 79.91; H, 14.06; Si, 6.03 percent, while the amount found was: C, 80.12; H, 14.15; Si, 5.92 percent.

EXAMPLE VII

Synthesis of Mixed R$_n$Si[CH$_2$CH$_2$SiR$^1$$_3$]$_{(4-n)}$ via Grignard Intermediate R,R$^1$=n-C$_8$H$_{17}$, n-C$_{10}$H$_{21}$ and n-C$_{12}$H$_{25}$, n=3

(10:70:20 molar ratio of n-C$_8$H$_{17}$Br:n-C$_{10}$H$_{21}$Br:n-C$_{12}$H$_{25}$Br)

A mixture of Grignard reagents was prepared in tetrahydrofuran by conventional technique using n-C$_8$H$_{17}$Br (14.5 g, 75.0 mmole), n-C$_{10}$H$_{21}$Br (116.1 g, 515 mmole), n-C$_{12}$H$_{25}$Br (37.4 g, 150 mmole), magnesium (20.5 g, 843 mmole) and anhydrous tetrahydrofuran (750 ml). To the above solution was added Cl$_3$SiCH$_2$CH$_2$SiCl$_3$ (28.0 g, 94.3 mmole) over a period of 15 minutes. The reaction mixture was then refluxed for 10 days. The mixture was cooled and then hydrolyzed by slowly pouring it into ice water. The mixture was filtered to remove excess Mg, the filtrate was acidified with diluted HCl, and 500 ml Et$_2$O was added. The organic layer was phase separated, washed with H$_2$O, and dried over MgSO$_4$. The solvent was removed by aspiration on a rotary evaporator to yield the crude product (121.6 g). The crude product was distilled to remove the low boiling components at <190° C./0.03 mmHg and the crude product (82.0 g) was then purified by column chromatography as described in Example I to yield mixed silahydrocarbons (69.0 g, colorless liquid).

EXAMPLE VIII

Some of the silahydrocarbons which were prepared as described above were characterized. Viscosity, low-pressure volatility using thermogravimetric analysis (TGA) and wear by Cameron-Plint were determined in order to compare with candidate space lubricants, Pennzane®. The procedure for the TGA of volatility characteristics included a sample size of 10 to 20 mg, a low pressure of 0.24 mmHg, and temperature of 25 to 600° C., programmed at 10° C. per minute. In order to compare the relative volatilities of the various polysilahydrocarbons and Pennzane®, two different data points were used. The two data points were T$_0$, the onset of volatilization temperature, and T$_{1/2}$, the temperature at which one-half of the fluid weight was lost. The lubricity characteristics of fluids were determined using the Cameron-Plint test. The Cameron-Plint tests were done with 52100 steel. The tests were done in nitrogen atmosphere and zero percent relative humidity. The following test conditions were used: Temperature: 150° C.; load: 250 Newton; stroke: 9 mm oscillation; cycle: 6 Hertz; sample: 1.5 to 2 ml; test time: 2 hours. During the test, friction, temperature and contact resistance were continuously monitored. After completion of the test, the wear area (mm$^2$) was calculated. All the results are listed in Table 1.

TABLE 1

PROPERTIES OF POLYSILAHYDROCARBONS AND PENNZANE ®

| Compound | Carbon No. | Kinematic Viscosity, mm/sec$^2$ | | | | | | Vacuum TGA at 0.24 mmHg | | Cameron Plint Wear Scar (mm$^2$) | | |
| --- | --- | --- | --- | --- | --- | --- | --- | --- | --- | --- | --- | --- |
| | | −54° C. | −40° C. | −17.8° C. | 0° C. | 40° C. | 100° C. | $T_0$ (° C.) | $T_{1/2}$ (° C.) | | | |
| CH$_3$Si[CH$_2$CH$_2$Si(C$_{10}$H$_{21}$)$_3$]$_3$ | 97 | No flow | 34910 | 3051 | 782 | 94.4 | 15.2 | 336 | 350 | 0.53 | 0.83 | 0.66 |
| CH$_3$Si[CH$_2$CH$_2$Si(C$_8$H$_{17}$)$_3$]$_3$ | 79 | 157,300 | 20780 | 2059 | — | 71.2 | 12.2 | 291 | 307 | | — | |
| CH$_3$Si[CH$_2$CH$_2$Si(C$_6$H$_{13}$)$_3$]$_3$ | 61 | 110,790 | 14870 | 1514 | 410 | 56.5 | 9.98 | 246 | 256 | | — | |
| C$_6$H$_9$[CH$_2$CH$_2$Si(C$_8$H$_{17}$)$_3$]$_3$ | 84 | — | 53230 | 4784 | 1187 | 121.1 | 17.43 | 280 | 292 | | — | |
| C$_6$H$_9$[CH$_2$CH$_2$Si(C$_6$H$_{13}$)$_3$]$_3$ | 66 | — | 51620 | 4700 | 954.5 | 112.3 | 15.83 | 265 | 277 | 1.16 | 0.58 | 0.67 |
| Pennzane ® | 65 | No flow | 77870 | 5158 | 1122 | 106 | 14.4 | 278 | 294 | 2.96 | 3.15 | 2.42 | 2.84 |

$T_0$: onset of volatilization temperature.
$T_{1/2}$: the temperature at which one-half of the fluid weight was lost.

One desirable property of an aerospace lubricant is low volatility to prevent it from boiling off in the vacuum of space. Low volatility is indicated by high values of $T_0$ and $T_{1/2}$ and high carbon numbers. Good flow properties at low temperatures, which are indicated by low kinematic viscosity values at −40° C., and if possible at −54° C., are also desirable. Another desirable property is low wear, shown by low numbers for Cameron Plint Wear Scale. As shown in Table I, the polysilylhydrocarbons of the present invention compare favorably with Pennzane® (three provide better properties, one comparable, and one slightly worse).

While certain representative embodiments and details have been shown for purposes of illustrating the invention, it will be apparent to those skilled in the art that various changes in the compositions and apparatus disclosed herein may be made without departing from the scope of the invention, which is defined in the appended claims.

What is claimed is:

1. A polysilahydrocarbon having a formula $$C_6H_{(12-m)}[CH_2CH_2SiR^1_3]_m$$

where $R^1$ is an alkyl group having from 6 to 18 carbon atoms, and "m" is an integer between 2 and 6.

2. A lubricant composition comprising a polysilahydrocarbon having a formula $$C_6H_{(12-m)}[CH_2CH_2SiR^1_3]_m$$

where $R^1$ is an alkyl group having from 6 to 18 carbon atoms, and "m" is an integer between 2 and 6.

3. A process for making a polysilahydrocarbon having a formula $$C_6H_{(12-m)}[CH_2CH_2SiR^1_3]_m$$

where $R^1$ is an alkyl group having from 6 to 18 carbon atoms, and "m" is an integer between 2 and 6, comprising:

reacting an alkyl silane having a formula H—Si—R$^1_3$ with a compound containing at least one vinyl group having a formula $$C_6H_{(12-m)}(CH=CH_2)_m$$

where $R^1$, and "m" are as defined above, in the presence of a catalyst.

4. The process of claim 3 wherein the catalyst is selected from transition metal salts and transition metal complexes.

5. The process of claim 4 wherein the catalyst is selected from platinum salts and platinum complexes.

6. The process of claim 5 wherein the catalyst is platinum acetylacetonate.

* * * * *